US00PP14345P29

(12) United States Plant Patent
Hanes

(10) Patent No.: US PP14,345 P2
(45) Date of Patent: Dec. 2, 2003

(54) PETUNIA PLANT NAMED 'JAM BLUIN'

(50) Latin Name: *Petunia hybrida*
Varietal Denomination: Jam Bluin

(75) Inventor: Mitchell Eugene Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 10/389,097
(22) Filed: Mar. 13, 2003
(51) Int. Cl.[7] ..... A01H 5/00
(52) U.S. Cl. ..... Plt./356
(58) Field of Search ..... Plt./356

*Primary Examiner*—Kent Bell
(74) *Attorney, Agent, or Firm*—Jondle & Associates, PC

(57) ABSTRACT

A petunia cultivar particularly distinguished by violet/blue colored flowers, compact habit and good basal branching.

1 Drawing Sheet

Genus and species: *Petunia hybrida.*
Variety denomination: 'Jam Bluin'.

BACKGROUND OF THE NEW PLANT

The present invention comprises a new and distinct cultivar of petunia, botanically known as *Petunia hybrida,* and hereinafter referred to by the cultivar name 'Jam Bluin'. The new cultivar is asexually reproduced from vegetative cuttings and tissue culture resulting from the cross of the seed/pod parent 'Spark Purple Vein', a commercial line that is unpatented×'Surfinia Blue Vein' a commercial line that is unpatented.

'Jam Bluin' is a product of a planned breeding program intended to create new petunia plants with violet/blue colored flowers, compact habit, good basal branching and moderately vigorous growth.

The new cultivar was created in 1999 in Gilroy Calif. and has been asexually reproduced repeatedly by vegetative cuttings and tissue culture in Gilroy, Calif., Andijk, The Netherlands, and Guatemala over a two and half year period. The plant has also been trialed at Gilroy, Calif. Litchfield, Mich. and Andijk, The Netherlands. The present invention has been found to retain its distinctive characteristics through successive asexual propagations; and this novelty is firmly fixed.

DESCRIPTION OF PHOTOGRAPH

This new petunia plant is illustrated by the accompanying photograph which shows blooms, buds, and foliage of the plant in full color, the colors shown being as true as can be reasonably obtained by conventional photographic procedures.

The photograph shows the mature flowers.

DESCRIPTION OF THE NEW CULTIVAR

The following detailed descriptions set forth the distinctive characteristics of 'Jam Bluin'. The data, which defines these characteristics, were collected from asexual reproductions carried out in Gilroy, Calif. The plant history was taken on 10 months old plants grown in one-gallon pots in fall/winter season, in a poly-covered greenhouse under 2–4 hours supplemental light and color readings were taken in the greenhouse in the winter season under natural light. Plants had been cut back numerous times prior to data readings being taken. Color references are primarily to The R.H.S. Colour Chart of The Royal Horticultural Society of London (R.H.S.). Texture description details were observed under a dissecting microscope according to The New Royal Horticultural Society Dictionary of Gardening (1992).

THE PLANT

Classification:
*Botanical.*—*Petunia hybrida.*
*Commercial.*—Petunia.
Form: Semi upright and decumbent.
Growth and branching habit: Good vigorous habit, well-branched, full plant.
Height: From soil level to top of blooms: Approximately 10–20 cm.
Width: Approximately 50–65 cm including flowers.
Time to produce a finished flowering plant: 9–11 weeks.
Outdoor plant performance: Full sun, free- flowering through the summer, some heat tolerance. Use in hanging baskets, mixed containers, window boxes and mass plantings.
Time to initiate roots: Approximately 18–23 days in the greenhouse.
Root description: Fibrous, white.

THE LEAVES

Arrangement: Alternate, upper leaves sub-opposite.
Length: 50–60 cm.
Width: 3.0–3.8 cm.
Leaf blade shape: Elliptic-Ovate.
Leaf margin: Entire.
Apex aspect: Acute/Obtuse.
Base aspect: Acuminate.
Leaf color: Upper side; RHS 137B (green); Underside; RHS 138A/B (green).
Texture: Sparse glandular hairs of various sizes.
Venation: Palmate.
Venation color: RHS 144A (yellow-green).
Petiole length: 0.9–1.2 cm.
Petiole width: 0.2 cm.
Petiole color: RHS 144A (yellow-green).
Petiole texture: Many glandular hairs of various sizes.

THE STEM

Length: 50–60 cm.
Diameter: 0.3–0.4 cm.
Internode length: 2.5–3.5 cm.
Color: RHS 144A (yellow-green).
Texture: Many glandular hairs of various sizes.
Stem anthocyanin: None.
Peduncle color: RHS 144A (yellow-green).
Peduncle length: 2.4–0.4 cm.
Peduncle diameter: 0.15–0.2 cm.
Peduncle texture: Many glandular hairs of various sizes.
Peduncle anthocyainin: Yes, reddish on upper side at calyx.

THE BUD

Shape: Oblong.
Diameter: 0.4–0.5 cm.
Length: 1.5–3.0 cm.
Color at tight bud: RHS 150C (yellow-green) base color; RHS 187A (greyed-purple) mid-veins.

THE FLOWER

Blooming habit: Continuous all through the growing season. Good floriferousness.
Inflorescence type: Flowers solitary in upper leaf axis.
Young flower color: close to RHS 76A/B (purple); RHS 83A (violet) mid-veins; RHS 77A (purple) secondary veining.
Young flower floret diameter: 5.0–5.6 cm.
Mature flower color: Upper side, RHS 76A/B (purple); RHS 83A (violet) mid-veins; RHS 77A (purple) and RHS 83A (violet) heavy secondary veining. Underside, RHS 85D (violet); subdued hue of RHS 177A (greyed-orange) mid-veins; very muted hue of RHS 77A (purple) secondary veins.
Corolla tube color inside: RHS 76A/B (purple) base color; RHS 77A (purple) mid-veins; RHS 83A (violet) heavy secondary veins.
Corolla tube length: 2.5–2.9 cm.
Corolla outside texture: Glandular hairs of various sizes.
Floret form and number of petals: Funnel form, 5 lobed petals fused at base.
Flower (limb) diameter: 5.0–6.0 cm.
Petal apex shape: Cuspidate.
Petal base shape: Fused.
Petal margin: Entire.
Waviness of petals: Weak.
Petal lobation: Moderate.
Petal texture: Papillose.
Sepals: 5.
Sepal color: RHS 137C (green).
Sepal length: 1.7–2.0 cm.
Sepal width: 0.4–0.7 cm.
Sepal shape: Oblong.
Sepal apex: Acute/Obtuse.
Sepal texture: Many glandular hairs of various sizes.
Lastingness of individual blooms: 4–8 days.
Fragrance: Fairly sweet.

THE REPRODUCTIVE ORGANS

Stamens: Five, 2 taller and 3 shorter.
Filament color: RHS N155D (white).
Pollen color: RHS 202B (black).
Pistil: One.
Stigma: RHS 194A (greyed-green).
Style color: RHS 194C (greyed-green).
Fruit seed set: Not observed.

DISEASE AND INSECT RESISTANCE

Not observed.

COMPARISON WITH KNOWN CULTIVARS

Compared to its female parent 'Spark Purple Vein' as follows: The female is later to flower and is less free flowering than 'Jam Bluin'. The female has a purple vein flower color and the 'Jam Bluin' has a violet/blue vein color.

Compared to its male parent 'Surfinia Blue Vein' as follows: The male parent is later to flower, has a darker green leaf and has fewer flowers in the center of the plant than does 'Jam Bluin'.

I claim:

1. A new and distinct petunia plant as shown and described herein.

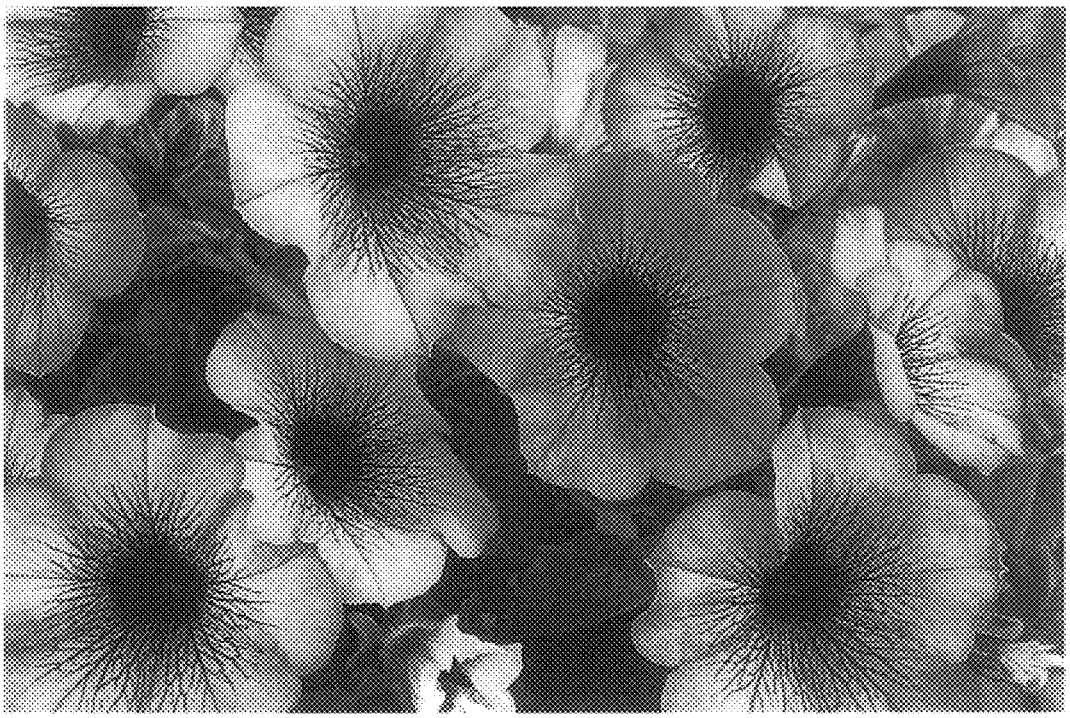

* * * * *